United States Patent
Hari

(10) Patent No.: US 11,622,516 B2
(45) Date of Patent: Apr. 11, 2023

(54) SELECTION OF NEW VARIETIES OF CANNABIS PLANTS EXPRESSING CANNABINOIDS BY CELL CULTURE

(71) Applicant: Bright Green Corporation, Wilmington, DE (US)

(72) Inventor: V. Hari, Orlando, FL (US)

(73) Assignee: Bright Green Corporation, East Windsor (CA)

( * ) Notice: Subject to any disclaimer, the term of this patent is extended or adjusted under 35 U.S.C. 154(b) by 279 days.

(21) Appl. No.: 16/594,715

(22) Filed: Oct. 7, 2019

(65) Prior Publication Data

US 2020/0107511 A1    Apr. 9, 2020

Related U.S. Application Data

(60) Provisional application No. 62/741,718, filed on Oct. 5, 2018.

(51) Int. Cl.
| | | |
|---|---|---|
| *A01H 4/00* | (2006.01) | |
| *A01H 6/28* | (2018.01) | |
| *A01G 22/00* | (2018.01) | |
| *A01G 9/029* | (2018.01) | |
| *A01G 2/00* | (2018.01) | |

(52) U.S. Cl.
CPC ............... *A01H 4/005* (2013.01); *A01G 2/00* (2018.02); *A01G 9/0291* (2018.02); *A01G 22/00* (2018.02); *A01H 6/28* (2018.05)

(58) Field of Classification Search
CPC .................................. A01H 4/50; A01H 4/005
See application file for complete search history.

(56) References Cited

PUBLICATIONS

Rai, M. K. et al., (2011) Environmental and Experimental Botany vol. 71, pp. 89-98. (Year: 2011).*
Binh, D.Q. (1992) Plant Cell Tissue Organ Cult. 29, pp. 75-82. (Year: 1992).*
Hussein, S., (2014) (Thesis: Cannabinoids production in *Cannabis sativa* L.: An in vitro approach; Technical University of Dortmund, 138 pages. (Year: 2014).*
Adhikari, D. et al. Frontiers in Plant Science; published Mar. 3, 2021, vol. 12, article 627240, pp. 1-22. (Year: 2021).*
Patel, P. (Fall 2019) Honors Thesis: Middle Tennessee State University, 24 pages. (Year: 2019).*
Feeney and Punja (2003) In Vitro Cell Dev Biol.—Plant 39:578-585. (Year: 2003).*
Jones, R. Aug. 1979; Masters Thesis: Cell Culture, Protoplast isolation, and Cell Fusion of *Cannabis sativa* L., University of Houston pp. 1-80. (Year: 1979).*

* cited by examiner

*Primary Examiner* — Russell Kallis
(74) *Attorney, Agent, or Firm* — Carlson, Gaskey & Olds, P.C.

(57) ABSTRACT

A method for generating new varieties of *Cannabis* plants with modified growth and cannabinoid phytochemical profiles includes subjecting plant parts of one or more *Cannabis* plants to pectinase digestion to release plant cells, centrifuging the released plant cells to obtain pelleted cells, and providing the pelleted cells on culture media. The pelleted cells are plated on a first culture media, which is a Murashige and Skoog or Gamborg B5 callus culture media.

9 Claims, No Drawings

SELECTION OF NEW VARIETIES OF CANNABIS PLANTS EXPRESSING CANNABINOIDS BY CELL CULTURE

CROSS-REFERENCE TO RELATED APPLICATIONS

This application claims priority to U.S. Provisional Application No. 62/741,718 which was filed on Oct. 5, 2018, and is incorporated herein by reference in its entirety.

BACKGROUND

*Cannabis sativa* is the single nomenclature name for all *cannabis* species including the tall growing hemp, the shorter variety *C. indica* and the short *C. ruderalis*. Other taxonomic classifications regard *C. sativa, C. indica* and *C. ruderalis* as independent species. All species are dioecious although monoecious varieties are known. While *C. sativa* and *C. indica* are short day plants, *C. ruderalis* is day neutral and is auto flowering. In general all species, sub species, varieties, strains, and eco-bio types of *cannabis* are recognized as belonging to three chemotaxonomic groups, namely those high in tetrahydrocannabinol (THC), those high in cannabidiol (CBD) and those that are intermediate.

SUMMARY

A method for generating new varieties of *Cannabis* plants with modified growth and cannabinoid phytochemical profiles includes subjecting plant parts of one or more *Cannabis* plants to pectinase digestion to release plant cells, centrifuging the released plant cells to obtain pelleted cells, and providing the pelleted cells on culture media. The pelleted cells are plated on a first culture media, which is a Murashige and Skoog or Gamborg B5 callus culture media.

The embodiments, examples, and alternatives of described in the claims and in the following description and drawings, including any of their various aspects or respective individual features, may be taken independently or in any combination. Features described in connection with one embodiment are applicable to all embodiments, unless such features are incompatible.

DETAILED DESCRIPTION

The present disclosure describes a process for the growth and selection of *Cannabis* plants exhibiting specific traits through an extensive cell and tissue culture process exploiting the inherent variability of individual cells in plants.

Example embodiments of this invention include tissue and cell culture methods for generating new varieties of *Cannabis* plants with modified growth and cannabinoid phytochemical profiles with emphasis on recovering short plants with ability to grow under controlled green-house hydroponic conditions.

Most *Cannabis* grown is from naturally occurring varieties which have been used as a base for classical Mendelian crossing to produce hybrids. Once a new hybrid or variety has been produced they are generally propagated by cloning or through seeds if seeds are true breeding.

The present disclosure provides a method of generating new morphological and chemotaxonomic varieties based on selection of plants from single cell cultures based on the knowledge that plant cells from the same plant are heterogeneous with respect to ploidy levels and gene expression resulting in variability. Thus, cells from different species, sub-species, varieties, strains, hybrids, bio-eco types of *C. sativa, C. indica* and *C. ruderalis* obtained by pectinase digestion of plant cells are cultured in culture media exposed to different environmental conditions such as temperature, light, oxygen and water stress in tissue culture environment chambers. This allows expression of cellular variability and cultures resulting from some cells to be different in gene expression. The surviving cultures are isolated and grown into callus, shoot, and root development through standard culture methods to select individual plants. These individual plants from each specific single cell background are grown and tested for: 1. growth characteristics (height, shrubby or bushy nature, response to water stress) 2. Cannabinoid profile, especially expression of CBD and THC. 3. Water stress response. 4. Temperature resistance. 5. Flowering time (e.g., short day, day neutral, long day).

An example method includes using cell and tissue culture methods for generating new varieties of *Cannabis* plants with modified growth and cannabinoid phytochemical profiles. Some embodiments are particularly useful for recovering short plants having an ability to grow under controlled green-house hydroponic conditions. In some embodiments, plants are selected for other parameters including water stress resistance, salinity, temperature resistance and flowering characteristics.

The example method begins with selecting starting plant material from at least one of *Cannabis sativa, C. indica*, and *C. ruderalis*, including all their sub species, varieties, strains, biotypes and ecotypes. The starting plant material is prepared by washing and disinfecting with 0.1% sodium hypochlorite, 70% ethanol, distilled sterile water. The washed plants are then vacuum-infiltrated with a solution of 1 mg/ml of pectinase in isotonic buffer under sterile conditions and incubated for 3 hrs. In some embodiments, the washing and vacuum-infiltration are performed in an automatic rotary shaker. Once prepared, differentiated mature leaves and floral parts are cut into approximately 1 cm pieces.

Pectinase digestion releases cells that are filtered through cheese cloth to remove debris. The filtered cells are centrifuged down in a clinical centrifuge at 500-1000 g. The cells are pelleted, then washed and re-suspended in a culture medium diluted in and plated onto Murashige and Skoog or Gamborg B5 callus culture media.

The cell culture plates are incubated in chambers that provide a light-controlled and temperature-controlled environment. Incubation may be performed under normal growth conditions to establish growth. The cells are then transferred to shoot and root inducing media. Cell culture plates are also incubated under water stress, different saline conditions, different temperatures, and other stresses. The cell types that demonstrate suitable or desirable survivor characteristics (e.g., cell survival) under such conditions are selected for further culture and growth.

Plantlets resulting from further culture and growth are then transferred to culture media in jars and planted into biodegradable pots in a nursery. In one example, the biodegradable pots are at least partially composed of peat moss and wood pulp (e.g., JIFFY-POTS®). The growth pattern of each plant and their individual cannabinoid profile is evaluated. Plants with short growth habits that contain high levels of CBD or THC (e.g., a level of CBD that exceeds a predefined threshold and/or a level of THC that exceeds a predefined threshold) or with desired ratios of CBD:THC are chosen for further propagation and maintenance. In one example, for medical marijuana a high level of CBD and a low level of THC is desirable. In one example, a plant is considered to have a "high level" of CBD if oils derived from the plant are composed of less than 0.3% THC with a remainder composed of CBD and/or other cannabinoids. In one example, the desired ratios of CBD:THC are ratios other than 24:1, 20:1, and 5:3.

Clones of selected plants are exposed to various types of stress based on different exposures to water, salinity, temperature, oxygen, and $CO_2$. The response of a plant that survives ands grow after being subjected to such stress provides indicators of desirable plant characteristics.

According to an example embodiment, those plants which combine short stature, desirable stress resistance (e.g., ability to grow under stress conditions), and desirable cannabinoid profiles and concentrations (e.g., desired CBD:THC ratios) are selected. The selected plants are maintained in a plant germplasm bank for propagation as desired.

Although example embodiments have been disclosed, a worker of ordinary skill in this art would recognize that certain modifications would come within the scope of this disclosure. For that reason, the following claims should be studied to determine the scope and content of this disclosure.

What is claimed is:

1. A method for *Cannabis* plants, comprising:
   subjecting plant parts of one or more *Cannabis* plants to pectinase digestion to release plant cells, wherein the pectinase digestion includes:
      vacuum-infiltrating the plant parts with a solution of approximately 1 mg/ml of pectinase in isotonic buffer under sterile conditions in an automatic rotary shaker; and
      incubating the pectinase solution that includes the plant parts for approximately 3 hours;
   centrifuging the released plant cells to obtain pelleted cells; and
   plating the pelleted cells on a first type of culture media, which is a Murashige and Skoog or Gamborg B5 callus culture media.

2. The method of claim 1, comprising, prior to the subjecting:
   cleansing the plant parts plants, said plant parts including mature leaves and floral parts; and
   cutting said plant parts into pieces of approximately 1 cm in length after said cleansing.

3. The method of claim 2, wherein said cleansing comprises:
   washing the plant parts; and
   disinfecting the plant parts with a solution including approximately 0.1% sodium hypochlorite, 70% ethanol, and distilled sterile water.

4. The method of claim 1, comprising, after said subjecting and prior to said centrifuging:
   filtering the released plant cells through cheese cloth to remove debris;
   wherein it is the filtered plant cells that are centrifuged to obtain the pelleted cells.

5. The method of claim 1, wherein said centrifuging is performed at 500-1000 G.

6. The method of claim 1, comprising:
   incubating the pelleted cells using different sets of growth conditions to establish growth; and
   transferring calli from the first type of culture media to a second type of culture media for additional growth.

7. The method of claim 6, wherein the second type of culture media is root and shoot media.

8. The method of claim 6, wherein said incubating the pelleted cells using different sets of growth conditions comprises:
   incubating a first portion of the pelleted cells under a first set of growth conditions; and
   incubating a second portion of the pelleted cells under a second set of growth conditions that differ from the first set of growth conditions and provide a greater degree of stress than the first set of growth conditions.

9. The method of claim 8, wherein the second set of growth conditions include at least one of water stress, saline conditions, and temperature conditions.

\* \* \* \* \*